United States Patent [19]

Sweet et al.

[11] Patent Number: 5,352,722

[45] Date of Patent: Oct. 4, 1994

[54] SILICONE PRESSURE SENSITIVE ADHESIVE CONTAINING ALKYLMETHYLSILOXANE WAX AND RELATED METHODS

[75] Inventors: Randall P. Sweet; Loren Durfee, both of Midland; Katherine L. Ulman, Sanford; Ross A. Noel, Midland, all of Mich.

[73] Assignee: Dow Corning Corporation, Midland, Mich.

[21] Appl. No.: 148,495

[22] Filed: Nov. 8, 1993

Related U.S. Application Data

[62] Division of Ser. No. 733,573, Jul. 22, 1991, Pat. No. 5,300,299.

[51] Int. Cl.$^5$ .................................................. C08K 5/54
[52] U.S. Cl. ............................. 524/266; 524/267; 524/268; 524/476; 428/343; 428/443; 428/447; 427/208.2; 427/208.4; 427/314; 427/334; 427/398.1; 424/448
[58] Field of Search .............. 428/447, 343, 443; 427/208.2, 208.4, 314, 334, 398.1; 524/266, 267, 268, , 476; 424/448

[56] References Cited

U.S. PATENT DOCUMENTS

| | | |
|---|---|---|
| 4,865,920 | 9/1989 | Sweet . |
| 4,882,377 | 11/1989 | Sweet et al. . |
| 4,883,669 | 11/1989 | Chien et al. . |
| 5,023,084 | 7/1991 | Chien et al. . |
| 5,147,916 | 9/1992 | Sweet .................... 524/266 |
| 5,162,410 | 11/1992 | Sweet .................... 524/266 |
| 5,246,997 | 9/1993 | Sweet .................... 524/266 |
| 5,290,564 | 3/1994 | Sweet .................... 424/448 |

FOREIGN PATENT DOCUMENTS 0443759 8/1991 European Pat. Off. .
0452034 10/1991 European Pat. Off. .

*Primary Examiner*—John Kight, III
*Assistant Examiner*—Duc Truong
*Attorney, Agent, or Firm*—Cargill and Bliss

[57] ABSTRACT

Hot-melt silicone pressure sensitive adhesive compositions containing alkylmethylsiloxane waxes and methods of using the compositions are disclosed. The hot-melt silicone pressure sensitive adhesive compositions include a mixture of (i) a silicate resin, (ii) a silicone fluid, and (iii) an alkylmethylsiloxane wax having a melting point of between 30° C. and 70° C. The alkylmethylsiloxane wax decreases dynamic viscosity of the adhesive compositions at temperatures ranging from about 50° C. to about 200° C.

10 Claims, 1 Drawing Sheet

SILICONE PRESSURE SENSITIVE ADHESIVE CONTAINING ALKYLMETHYLSILOXANE WAX AND RELATED METHODS

This is a division of U.S. patent application Ser. No. 07/733,573, filed Jul. 22, 1991, now U.S. Pat. No. 5,300,299.

TECHNICAL FIELD

The present invention relates to hot-melt silicone pressure sensitive adhesive compositions containing alkylmethylsiloxane wax and methods of using the composition.

BACKGROUND OF THE INVENTION

A pressure sensitive adhesive, generally, is a material which adheres to a surface with slight pressure and releases from the surface with negligible transfer of the material to the surface. Silicone pressure sensitive adhesives that are known in the art are typically solvent-based adhesives. The solvents are employed primarily to reduce the dynamic viscosity of the silicone pressure sensitive adhesive to a dynamic viscosity which is easily coated onto the substrate of choice, and the solvents are removed after coating. As with any solvent-based pressure sensitive adhesive (PSA), special precautions must be taken to contain and avoid environmental exposure of the solvents and avoid flammable and explosive conditions as many of the solvents used are flammable.

Hot-melt pressure sensitive adhesives are those adhesives, which upon heating, melt to viscosities suitable for coating, but when cooled are generally in a flowless state. Hot-melt pressure sensitive adhesives exhibit the following advantages over solvent-based pressure sensitive adhesives. Hot-melt pressure sensitive adhesives: (1) do not require removal and containment of solvents; (2) due to the absence of flammable solvents, do not require special precautions to avoid fires; (3) make available coating processes other than those commonly used with solvent-based pressure sensitive and (4) are more easily coated into thick sections with minimal bubbling, a problem which often results with coating out solvent-based PSA's. In addition, hot-melt PSA's have the advantage of not containing solvents which sometimes interfere with the addition of other ingredients to the PSA.

Silicone pressure sensitive adhesives are preferred over other types of PSA's in many applications, especially in the medical area. For example, because silicone pressure sensitive adhesives are acceptable for topical use, they have found use in transdermal drug delivery applications which involve the adherence of a drug-containing patch to a patient's skin.

U.S. Pat. No. 4,865,920 to Randall P. Sweet, discloses a method of making hot-melt silicone pressure sensitive adhesives which have the inherent benefits of being composed of silicone and being a hot-melt PSA. In U.S. Pat. No. 4,865,920, the hot-melt silicone pressure adhesive composition consists of (i) a silicate resin; (ii) a silicone fluid; and (iii) 1 to 10 weight percent, based on the total weight of the silicate resin and silicone fluid, of an ester having the formula: R—C(O)OR' wherein R is a monovalent hydrocarbon radical having from 2 to 32 carbon atoms and R' is a monovalent hydrocarbon radical having from 1 to 14 carbon atoms.

Although this silicone pressure sensitive adhesive composition has been found to be highly efficacious, it would be desirable to include additives which will decrease dynamic viscosity to improve the coatability of the hot-melt adhesive at temperatures at or below 200° C.

It would also be desirable for the adhesive to be compatible with a variety of release liners. The new hot-melt silicone pressure sensitive adhesive must allow permeation of lipophilic drugs through the PSA. Also, the adhesive should have controllable adhesion, so that the aggressiveness of adhesion can be tailored to the application.

Therefore, it is a primary object of the present invention to teach a composition for a silicone pressure sensitive adhesive which includes an alkylmethylsiloxane wax in combination with a silicate resin and a silicone fluid which will decrease the dynamic viscosity of the adhesive so that coating is easier to achieve.

It is another object of the present invention to provide a method for coating the wax-containing pressure sensitive adhesive onto a substrate.

SUMMARY OF THE INVENTION

This invention provides a hot-melt pressure sensitive adhesive composition which is formed of materials which are highly acceptable in topical applications. The hot-melt silicone pressure sensitive adhesive compositions of this invention contain an alkylmethylsiloxane wax which renders the adhesive less viscous at temperatures up to about 200° C. and therefore improves adhesive coatability over the prior art silicone PSA's and the hot-melt PSA of U.S. Pat. No. 4,865,920. The invention also provides a means of controlling the pressure sensitive adhesive properties of tack, adhesion, and release of the composition.

The hot-melt silicone pressure sensitive adhesive composition comprises a mixture of (i) a silicate resin and (ii) a silicone fluid, the mixture exhibiting tackiness and adhesiveness, the mixture being blended with (iii) an alkylmethylsiloxane wax which decreases the dynamic viscosity of the adhesive at the temperatures used for coating the adhesive onto a substrate. Improved adhesive coatability minimizes waste of materials during manufacture and expedites production. This results in cost savings and increases profits. The invention also encompasses methods of using the composition.

These and other objects and advantages of the invention will become more apparent from a detailed description thereof which follows.

DETAILED DESCRIPTION OF THE INVENTION

Figure 1:
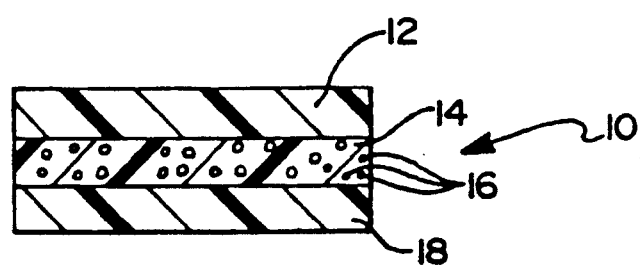
FIG. 1 shows a matrix-type delivery device for a bioactive agent or drug in place within a transdermal patch.

Generally, the hot-melt compositions made in accordance with the present invention are composed of a silicone pressure sensitive adhesive containing (i) a silicate resin present in an amount between about 30 to about 70 percent by weight based on total composition weight, (ii) a silicone fluid present in an amount between about 22 to about 60 percent by weight based on total composition weight, and (iii) an alkylmethylsiloxane wax present in an amount between about 1.0 to about 25.0 percent by weight based on total composition weight.

The following paragraphs disclose acceptable and preferable silicone pressure sensitive adhesives which may be combined with the disclosed alkylmethylsiloxane waxes to provide an improved hot-melt adhesive combination with decreased dynamic viscosity. This improved adhesive may be used, in turn, to form improved devices for many applications including transdermal drug delivery patches and other medical applications which do not require solvents for coating the adhesive.

As mentioned above, hot-melt PSA's are preferred over previously available adhesives because solvents are not required to coat the adhesive on a substrate (e.g. a bandage or patch). It appears that the addition of alkylmethylsiloxane waxes to a basic PSA formulation helps to decrease dynamic viscosity and allows it to be hot melt coated. This means that the coatability of the PSA in the absence of solvents is improved, and better devices can be made. One of ordinary skill in the art will clearly see the advantages of the present invention.

I. Suitable Silicone Pressure Sensitive Adhesives

One suitable class of pressure sensitive adhesives to be employed in the hot-melt compositions of this invention consists of a mixture of (i) a trimethylsilyl-endblocked polysilicate resin such as a silicate resin, consisting of a benzene-soluble resinous copolymer containing silicon-bonded hydroxyl radicals and consisting essentially of triorganosiloxy units of the formula $R_3SiO_{\frac{1}{2}}$ and tetra functional siloxy units of the formula $SiO_{4/2}$ in a ratio of about 0.6 to 0.9 triorganosiloxy units for each tetra functional siloxy unit present in the copolymer, wherein each R is a monovalent alkylmethylsiloxane radical independently selected from the group consisting of hydrocarbon radicals of from 1 to 6 inclusive carbon atoms; and (ii) a silanol-endstopped polydiorganosiloxane fluid, e.g. a polydimethylsiloxane fluid. U.S. Pat. No. 2,736,721 to Dexter, et al. and U.S. Pat. No. 2,814,601, to Currie, et al. are hereby incorporated by reference to teach of such or similar pressure sensitive adhesive compositions.

Another class of suitable pressure sensitive adhesives for use in combining with the alkylmethylsiloxane wax according to the present invention is that or those similar to U.S. Pat. No. 2,857,356, to Goodwin, Jr., which is hereby incorporated by reference. The Goodwin, Jr. patent teaches silicone pressure sensitive adhesives which consist of a mixture of ingredients comprising (i) a cohydrolysis product of a trialkyl hydrolyzable silane and alkyl silicate, wherein the cohydrolysis product contains a plurality of silicon-bonded hydroxy groups, and (ii) a linear, high dynamic viscosity organopolysiloxane fluid containing silicon-bonded hydroxy groups.

To practice the present invention the silicate resin (i) and the silicone fluid (ii) may optionally be condensed together according to a procedure such as the procedure described in Canadian Patent 711,756 to Pail, which patent is hereby incorporated by reference. In such a condensation reaction, the silicate resin (i) and the silicone fluid (ii) are mixed together in the presence of a catalytic amount of a silanol condensation catalyst, and then the silicate resin (i) and the silicone fluid (ii) are condensed, for example, by heating under reflux conditions for 1 to 20 hours. Examples of silanol condensation catalysts are primary, secondary, and tertiary amines, carboxylic acids of these amines and quaternary ammonium salts.

Another class of suitable pressure sensitive adhesives to use in combination with the alkylmethylsiloxane waxes are those compositions described in U.S. Pat. Nos. 4,591,622 and 4,584,355 to Blizzard et al., U.S. Pat. No. 4,585,836 to Homan et al., and U.S. Pat. No. 4,655,767 to Woodard et al., which patents are also hereby incorporated by reference. Generally, these pressure sensitive adhesives consist of a blend of (i) a silicate resin and (ii) a silicone fluid which are chemically treated to reduce the silicone bonded hydroxyl content of the blend. These adhesives may optionally be condensed as described immediately above prior to the chemical treatment.

Typically, the most practical pressure sensitive adhesive to combine with an alkylmethylsiloxane wax contains at least 100 ppm silanol radicals and preferably between about 200 ppm and 1,200 ppm of silanol radicals, and includes a silicate resin combined with a silicone fluid as described above. The silicate resin preferably has a molecular weight ranging from about 3500 to about 7000, and is employed in amounts from about 30 to about 70 percent by weight based on the total resultant composition of the silicone pressure sensitive adhesive. The silicone fluid is preferably employed from about 22 to about 60 percent by weight, wherein the total parts of the silicate resin and the silicone fluid equal 100 percent. It is usually preferred that the ratio of silicate resin to silicone fluid is between about 2:3 and about 3:7.

The silicone pressure sensitive adhesives used in this invention are not considered to be "silicone rubbers", which generally refer to non-tacky vulcanized rubbers. The most common type of silicone rubber consists of a mixture of a polydimethylsiloxane gum, a filler (such as fumed silica or other inorganic, non-resinous material), or a crosslinker, and optionally, a catalyst. On the other hand, the silicone pressure sensitive adhesives employed in this invention are tacky (or sticky) to the touch without the addition of plasticizers and typically adhere to a substrate after mild pressure is applied. The silicone pressure sensitive adhesives may be cured or "rubberized" after being mixed with a cohesive strengthening agent as discussed below. However, even after curing, the silicone pressure sensitive adhesive composition remains tacky.

The process of curing or crosslinking silicone pressure sensitive adhesives is known in the art. For example, see "Silicone Pressure Sensitive Adhesives" by D. F. Merrill in the *Handbook Of Pressure Sensitive Adhesive Technology*, edited by D. Satas (Van Nostrand Reinhold, Florence, Ky., 1982), pages 344–352 and "Formulating Silicone Pressure Sensitive Adhesives For Application Performances" by L. A. Sobieski in *Making It Stick in '86, Advances In Pressure Sensitive Tape Technology*, seminar proceedings (Pressure Sensitive Tape Council, Deerfield, Ill., 1986), pages 1–5, both sources being hereby incorporated by reference.

Generally, however, for drug delivery applications, the silicone pressure sensitive adhesive compositions are not crosslinked because either (1) the crosslinking temperature is too high for the drugs or (2) the additives needed for crosslinking are non-biocompatible ingredients. A silicone pressure sensitive adhesive composition is generally considered not crosslinked if it can be dissolved in a solvent.

Another difference between silicone pressure sensitive adhesives suitable for use in the present and silicone rubbers, which are unsuitable, lies in the fact that silicone pressure sensitive adhesives are usually fillerless or contain low amounts, e.g., less than about 5 weight %, of fillers, such as fumed silica or other inorganic reinforcing fillers known in the silicone art. On the other hand, silicone rubbers typically contain about 15–35 weight % filler. Fillers are usually not desired in high quantities in silicone pressure sensitive adhesives, because high quantities often cause the silicone pressure sensitive adhesives to lose tack and adhesiveness and to increase in dynamic viscosity, making it more difficult to apply a coating of the silicone pressure sensitive adhesive.

The silicone PSA's described above are all suitable for combining with certain alkylmethylsiloxane waxes, as described in the following paragraphs. These alkylmethylsiloxane waxes, when combined with the PSA's provide adhesives which exhibit decreased dynamic viscosity, and improved coatability without solvents.

II. The Alkylmethylsiloxane Waxes

The alkylmethylsiloxane waxes suitable for use in the present invention include waxes having the following formulations:

(RMeSiO)$_x$ wherein R is $C_nH_{2n+1}$, Me is $CH_3$, $14 \leq n \leq 28$, and X is an integer from 4 to 6;

RMe$_2$SiOSiMe$_2$R wherein Me is $CH_3$, R is $C_nH_{2n+1}$, and $n \geq 18$;

RMe$_2$SiOSiMe$_3$ wherein Me is $CH_3$, R is $C_nH_{2n+1}$, and $n \geq 24$;

RMeSi(OSiMe$_3$)$_2$ wherein Me is $CH_3$, R is $C_nH_{2n+1}$, and $n \geq 24$;

Me$_3$SiO(RMeSiO)$_x$(R'MeSiO)$_y$SiMe$_3$ wherein Me is $CH_3$, R is $C_nH_{2n+1}$, and $n \geq 18$, R' is H or $C_nH_{2n+1}$ and $n \geq 1$, when R' is H or $CH_3$ then the ratio of X:Y is greater than 1:3;

RSiO$_{3/2}$ wherein R is $C_nH_{2n+1}$, and $n \geq 1$; and mixtures thereof.

The alkylmethylsiloxane waxes of the present invention have a melting point of between about 30° C. and about 70° C.

Preferably, the alkylmethylsiloxane wax is added in an amount between about 1.0 and about 25.0 percent by weight based on total composition weight. Best results are noted when the wax is utilized in an amount between about 5 percent and about 15 percent by weight based on total composition weight.

The alkylmethylsiloxane wax functions to decrease the dynamic viscosity of the hot-melt pressure sensitive adhesive at temperatures equal to or less than 200° C. Desirable dynamic viscosities of the wax-containing adhesives at temperatures equal to or less than 200° C. are less than or equal to 800 poise. The wax is particularly effective at temperatures of between about 85° C. and 200° C. to improve the coatability of the adhesive onto a substrate. This effect is shown in Table 2.

The hot-melt silicone pressure sensitive adhesive compositions described herein are prepared by mixing (i) silicate resin and (ii) silicone fluid with (iii) the alkylmethylsiloxane wax at a temperature of at least 85° C. Alternatively, the wax may be dissolved in solvent added to the silicate resin and silicone fluid mixture and thereafter the solvent may be removed from the mixture. The hot-melt silicone pressure sensitive adhesive compositions are then heated to a coatable dynamic viscosity, to temperatures of between about 85° C. and 200° C. and coated on a substrate The adhesive coated substrate is then cooled until it is in a non-flowing state.

A method of coating a hot-melt, alkylmethylsiloxane wax-containing, silicone pressure sensitive adhesive composition onto a substrate includes first preparing the hot-melt silicone pressure sensitive adhesive by mixing together (1) a silicate resin, (2) a silicone fluid, and (3) an alkylmethylsiloxane wax present in an amount between about 5 and about 15 percent by weight based on total adhesive composition weight, which decreases dynamic viscosity of the resultant hot-melt adhesive at temperatures, ranging from about 50° C. to about 200° C. Thereafter, the mixture is heated to a coatable temperature of between about 85° C. and 200° C., and coated onto a substrate.

The hot-melt silicone pressure sensitive adhesive compositions may be coated onto the substrate, or other backing, by using any conventional means, such as roller coating, dip coating, extrusion, knife coating, or spray coating. Although the hot-melt silicone pressure sensitive adhesive compositions of the invention are preferably adhered to a bandage or patch for medical applications, they will also adhere to many substrates, such as paper, cloth, glass cloth, silicone rubber, polyethylene, polyethylene terephthalate, polytetrafluoroethylene, glass, wood, metals, and skin. After coating, the PSA is cooled until it is in a non-flowing state. The alkylmethylsiloxane waxes used in this method are those listed hereinabove. The preferred weight percents of the components were also described above.

Therefore, the following suggested uses and examples should not be used to limit the invention. Depending on the desired use, it may be desirable to apply adhesion promoters on the substrate surface upon which the hot-melt silicone pressure sensitive adhesive composition will be placed.

III. Devices Utilizing Adhesive

The hot-melt silicone pressure sensitive adhesive compositions containing alkylmethylsiloxane waxes as taught by this invention are especially suitable for assisting in delivering a bioactive agent, such as a drug, to a bioactive agent-accepting substrate, such as a patient's skin. The hot-melt silicone pressure sensitive adhesive compositions of this invention may be employed in three types of bioactive agent delivery modes.

The first mode is a matrix-type of delivery device for a bioactive agent or drug. As shown in FIG. 1, device 10 comprises at least three layers, including a backing substrate 12 which may be permeable or occlusive to water vapor transmission from skin; a matrix 14, which is between about 1 and 15 mils thick, atop at least portions of the backing substrate and containing a silicone pressure sensitive adhesive which includes the alkylmethylsiloxane wax, and additionally including drugs, excipients, enhancers, co-solvents 16 or mixtures thereof, said adhesive being compatible with the drugs, excipients, enhancers and co-solvents; and a pressure sensitive adhesive release liner 18.

The matrix-type transdermal drug delivery device as shown in FIG. 1 may include various drugs selected from the group consisting of cardiovascular agents, antiarrhythmic agents, antianginal agents, antibiotics, antifungals, antimicrobials, antihypertensives, analgesics, local anesthetics, contraceptives, hormonal supplements, anti-smoking agents, appetite suppressants, hypnotics, anxiolytics and mixtures thereof.

The matrix-type transdermal drug delivery device may also include co-solvents, enhancers and excipients as described above. These compounds may be selected from the group consisting of fatty acid esters, polyols, surfactants, terpenes, glycerol esters, polyethylene glycol esters, amides, sulfoxides, lactams, nonionic surfactants, sorbitan esters, and mixtures thereof.

Figure 2:
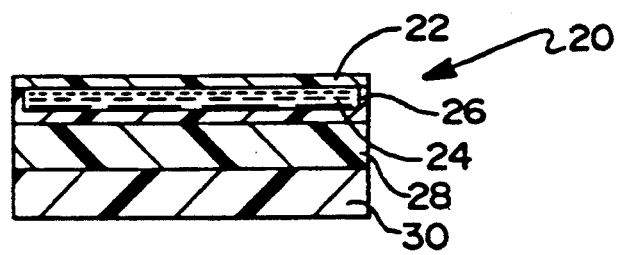
FIG. 2 shows a liquid reservoir-type transdermal drug delivery device.

As shown in FIG. 2, the second mode of delivery is a reservoir-type transdermal drug delivery tape device. FIG. 2 shows a liquid-containing reservoir-type drug delivery device, generally denoted as numeral 20, which comprises a minimum of five layers from top to bottom. The first layer 22 is a backing substrate. The second layer includes a liquid reservoir 24 which may contain bioactive agents or other compositions selected from the group consisting of drugs, enhancers, excipients and co-solvents and mixtures thereof. The third layer 26 is a rate controlling membrane positioned such that the reservoir 24 is sealed between the backing substrate 22 and the rate controlling membrane 26. This membrane acts as the rate controlling mechanism for the delivery of the liquid from the reservoir 24 to the patient. The fourth layer 28 is a hot-melt, alkylmethylsiloxane wax-containing pressure sensitive adhesive coated on top of the previous layers, and the adhesive should be compatible with any of the drugs, excipients, enhancers, and co-solvents present in the liquid reservoir. Appropriate alkylmethylsiloxane waxes for this device are described hereinabove. The fifth layer 30 is a release liner attached on top of the adhesive layer, averaging between about 1 and 15 mils thick and preferably between about 1 and 3 mils thick.

After removing the release liner, this device may be adhered to a surface, such as a patient's skin. Once in place, the device 20 allows the bioactive agent of liquid reservoir 24 to pass from the reservoir through the attached rate controlling membrane 26 and adhesive layer 28 into the skin of the patient. The reservoir 24 of the transdermal drug delivery device may include drugs selected from the group consisting of cardiovascular agents, antiarrhythmic agents, antianginal agents, antibiotics, antifungals, antimicrobials, antihypertensives, analgesics, local anesthetics, contraceptives, hormonal supplements, anti-smoking agents, appetite suppressants, hypnotics, anxiolytics and mixtures thereof.

The adhesive layer of the liquid reservoir-type transdermal drug delivery device may include the co-solvents, enhancers and excipients which are selected from the group consisting of fatty acid esters, polyols, surfactants, terpenes, glycerol esters, polyethylene glycol esters, amides, sulfoxides, lactams, nonionic surfactants, sorbitan esters, and mixtures thereof.

Figure 3:
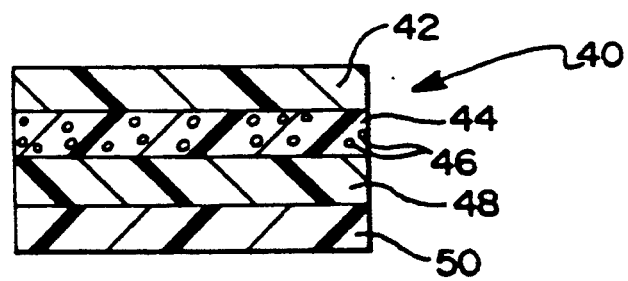
FIG. 3 shows a solid state reservoir-type transdermal drug delivery device.

The third mode of delivery is a solid state reservoir transdermal drug delivery device denoted by numeral 40, shown in FIG. 3. This device includes a first layer 42 which is a backing substrate. The second layer constitutes a solid reservoir 44 which may contain one or more bioactive agents or other compositions selected from the group consisting of drugs, excipients, enhancers, and co-solvents indicated as 46. The third layer is a hot-melt alkylmethylsiloxane wax-containing pressure sensitive adhesive layer 48 which is compatible with the drugs, excipients, enhancers and co-solvents contained therein. Again, appropriate alkylmethylsiloxane waxes for this device are described hereinabove.

The pressure sensitive adhesive layer of this solid state device averages between about 1 and 15 mils thick, and preferably is between 1 and 3 mils thick. The fourth layer is a release liner 50. If desired, an additional layer (not shown) comprising a rate controlling membrane may be positioned between the solid reservoir 44 and the PSA 48. The solid reservoir 44 may contain drugs as described above for the liquid reservoir device of FIG. 2.

The following examples of the invention are meant to be illustrative only and should not be construed as limiting the invention which is properly delineated in the appended claims. In the following examples, all parts and percentages are by weight unless otherwise specified.

IV. EXAMPLES

Described below is a basic silicone pressure sensitive adhesive prepared without the alkylmethylsiloxane waxes as called for by the present invention. This is indicated in the Examples as the control sample, Control PSA. From this basic formulation, examples were prepared by adding various alkylmethylsiloxane waxes, testing them and tabulating the results.

The basic adhesive formulation included two main components: a silicate resin and a silicone fluid. The Control PSA, was made from a various combination of Resins A-1, A-2 and trimethylsiloxy endblocked polydimethylsiloxane (PDMS) Fluid A as described below.

For the following examples, Resin A-1 is a xylene solution of a resinous copolymeric siloxane prepared from 45 parts of sodium silicate (41.6⁰ Be) and 20 parts of $Me_3SiCl$ ($Me=CH_3$) according to the method of U.S. Pat. No. 2,676,182 to Daudt, et al., which is hereby incorporated by reference, and contains $Me_3SiO_{\frac{1}{2}}$ units and $SiO_{4/2}$ units in a ratio of approximately 0.75:1.0, and has a non-volatile content (N.V.C.) of typically about 69–71%, an acid number in the range of 0.3 to 1.4, a dynamic viscosity value in the range of 10–14 centipoise at 25° C. at 60% N.V.C. in xylene solution, and a silicon-bonded hydroxyl content of about 2.5 weight percent based on a 100% N.V.C.

Resin A-2 is devolatilized Resin A-1 (100% non-volatile content).

PDMS Fluid A is a homogeneous mixture of a hydroxyl-endblocked polydimethylsiloxane having a number-average molecular weight of approximately 40,000, along with minor amounts of cyclic polydimethylsiloxane having degrees of polymerization between 4 and 30, the mixture having a dynamic viscosity between 12,000 and 15,000 centipoise as measured using a Brookfield Viscometer Model HAF with spindle #3 at 10 RPM's.

The Control PSA was prepared by homogeneously mixing 24.1 parts by weight of Resin A-2, 39.8 parts by weight xylene, and 36.1 parts by weight PDMS Fluid A. The mixture was then heated to 115° C. and anhydrous ammonia was passed through the mixture at a rate of 11 ml/min/lb of non-volatile component of the mixture for approximately 4 hours. To endcap the mixture, hexamethyldisilazane was then mixed at a 3:1 mole ratio of endblocking triorganosilyl to total silicon-bonded hydroxyl radicals present in the resin copolymer and polydiorganosiloxane, and the mixture was allowed to react for 3 hours at 95°–100° C. The mixture was then heated to 140° C. and maintained at 140° C. under reflux conditions for 3 hours to remove condensation water.

The physical properties of tack, release, adhesion and shear are set forth in Table 1. The methods for measuring these values are described here. Although the following Examples utilize different chemical compositions, the same testing methods were followed for all samples. Measurements were obtained by testing a one inch wide polyester tape having a silicone pressure sensitive adhesive thereon. The adhesives were prepared by blending about 1.0 percent to 15.0 percent by weight of an alkylmethylsiloxane wax with between 99.0 and 85.0 percent by weight of silicone pressure sensitive adhesive and casting it to about a 2 mil thickness on "SCOTCH-PAK" 1022 Release Liner, a polyester film coated with a release coating available from the 3M Company, St. Paul, Minn., owner of the trademark "SCOTCH-PAK", 3M Company Health Care Specialties Div. St. Paul Minn. After coating, a "MYLAR" polyester film was adhered to each casted alkylmethylsiloxane wax-containing sample with a 4 lb. rubber transfer roller.

The laminate is then cut into one-inch wide strips with the use of a one-inch tape specimen cutter received from the Pressure Sensitive Tape Council, 1800 Pickwick Ave., Glenview, Ill. 60025-1357.

The tack values were measured using a "POLYKEN" Probe Tack Tester, Series 400, made by Testing Machines, Inc., Amityville, N.Y. The speed of the probe was controlled at 0.5 cm/second and dwell time was at 0.5 seconds. Tack values of between about 50 and about 800 grams/cm$^2$ are considered acceptable.

The release values were obtained by stripping the tape from the "SCOTCH-PAK" 1022 Release Liner at a rate of 40 inches/minute at an angle of 180° while attached to a tensile testing machine. An average value over the entire length of the liner was recorded. Release values of less than 50 gm/cm are considered acceptable.

The adhesion values were obtained as follows. The tapes having the silicone pressure sensitive adhesive composition thereon were adhered to a stainless steel panel with a 4 lb. roller and allowed to rest for 20 minutes. The adhesion measurements were obtained by stripping each tape from the panel at a rate of 12 inches/minute at an angle of 180° while attached to a tensile testing machine. Desirable values range between about 100 and about 2000 gm/cm.

Shear values were measured by cutting three strips of the prepared laminates 2.5 cm wide and 7.5 cm in length. A 3.5 cm wide by 5.0 cm long strip of Mylar, a polyester film available from DuPont de Nemours, E. I. Co., Wilmington Del. also owner of the trademark "Mylar", is applied to the adhesive strip so as to provide an overlap of 2.5 cm in the lengthwise direction. These are laminated using a 4 lb. rubber roller and allowed to equilibrate for 20 minutes. The specimen is mounted into the jaws of an Instron Model 1122 Tensometer, available from Instron Corporation, and pulled at a speed of 0.5 cm/min. and the peak load required to shear and separate the laminate is recorded in Kg/6.25 cm$^2$. Desirable values range between 4 and 20 kg/6.25 cm$^2$.

Dynamic viscosities (n*) measured in poise and elastic storage moduli (G') measured in dynes/cm$^2$ were measured on the adhesive compositions using a Rheometrics ® Dynamic Spectrometer, Model RDS2 available from Rheometrics, Piscataway, N.J., and running a temperature sweep on 4 gram samples of 1 mm thickness, and operating the tester at a frequency of 100 radians/sec and a 1% strain using a 50 mm cup and plate. Desirable dynamic viscosities (n*) should be less than or equal to 800 poise at or below 200° C.

Elastic storage modulus (G') is directly related to die swell and elastic memory. The higher the die swell, the smaller the size of an orifice required for a given coating thickness. Therefore, the lower the elastic storage modulus, the better, as it is then easier to coat onto a substrate. Tests similar to those run in these examples are described in ASTM 4065-82. Desirable storage modulus values should be less than 45,000 dynes/cm$^2$ at or below 200° C.

Hereinbelow, the term "pressure sensitive adhesive" may be abbreviated to "PSA".

Example 1

Adhesive formulations combining Control PSA and varying amounts of alkylmethylsiloxane waxes were prepared as set forth in Tables 1–2. As shown in Table 1, these adhesive preparations were evaluated for physical properties of tack, release, adhesion and shear. Tack values ranged between 5 and 521 gm/cm$^2$, and 11 of 12 samples were well within the acceptable range of 50 to 800 gm/cm$^2$. Release values ranged between 2.1 and 17.3 gm/cm, and all samples were within the acceptable range of less than or equal to 50 gm/cm. Adhesion values for our samples ranged between 186 and 790 gm/cm. All samples were within the acceptable range of 100–2000 gm/cm. Shear values ranged from 5.1 to 15.3 kg/6.25 cm$^2$ and were within the acceptable range of 4 to 20 kg/6.25 cm$^2$. These results show that the addition of siloxane waxes to the PSA's does not adversely affect the physical properties of the PSA's.

Decreased dynamic viscosity values are desirable to improve coatability without solvents. Each sample containing the alkylmethylsiloxane wax demonstrated the desirable result of decreasing dynamic viscosity in comparison to the Control PSA.

TABLE 1

| | Physical Data For Control PSA With Alkylmethylsiloxane Waxes | | | | | | |
|---|---|---|---|---|---|---|---|
| Wax Product | Wax MP | Wt % Wax | Thick (mils) | Tack (g/cm$^2$) | Release (g/cm) | Adhesion (g/cm) | Shear Kg/6.25 cm$^2$ |
| Control PSA | — | 0 | 2 | 377 | 3.2 | 573 | 15.8 |
| (C$_{18}$H$_{32}$SiO)$_4$ | 38° C. | 1% | 3.5 | 366 | 2.9 | 783 | 13.7 |
| (C$_{18}$H$_{32}$SiO)$_4$ | 38° C. | 5% | 3 | 521 | 5.7 | 495 | 13.2 |
| (C$_{18}$H$_{32}$SiO)$_4$ | 38° C. | 10% | 2.5 | — | 8.6 | 186 | — |
| (C$_{18}$H$_{32}$SiO)$_4$ | 38° C. | 15% | 4.3 | 189 | 5 | 611 | 11.8 |
| (C$_{20}$H$_{34}$SiO)$_5$ | 53° C. | 1% | 3 | 210 | 2.1 | 790 | 14.8 |

TABLE 1-continued

Physical Data For Control PSA With Alkylmethylsiloxane Waxes

| Wax Product | Wax MP | Wt % Wax | Thick (mils) | Tack (g/cm$^2$) | Release (g/cm) | Adhesion (g/cm) | Shear Kg/6.25 cm$^2$ |
|---|---|---|---|---|---|---|---|
| (C$_{20}$H$_{34}$SiO)$_5$ | 53° C. | 5% | 4.5 | 163 | 2.5 | 621 | 13.5 |
| (C$_{20}$H$_{34}$SiO)$_5$ | 53° C. | 10% | 2.5 | — | 10.3 | 397 | — |
| (C$_{20}$H$_{34}$SiO)$_5$ | 53° C. | 15% | 6.5 | 154 | 17.2 | 560 | 5.1 |
| (C$_{24-28}$H$_{49-57}$MeSiO)$_5$ | 56° C. | 1% | 4 | 367 | 2.2 | 772 | 15.3 |
| (C$_{24-28}$H$_{49-57}$MeSiO)$_5$ | 56° C. | 5% | 3.5 | 109 | 2.9 | 654 | 14.5 |
| (C$_{24-28}$H$_{49-57}$MeSiO)$_5$ | 56° C. | 10% | 2.5 | — | 12 | 438 | — |
| (C$_{24-28}$H$_{49-57}$MeSiO)$_5$ | 56° C. | 15% | 3.5 | 601 | 17.3 | 328 | 5.8 |
| Me$_3$SiO(C$_{18}$H$_{37}$MeSiO)$_{54}$-(MeHSiO)$_{18}$SiMe$_3$ | 48° C. | 1% | 3 | 202 | 3.2 | 639 | 14.6 |
| Me$_3$SiO(C$_{18}$H$_{37}$MeSiO)$_{54}$-(MeHSiO)$_{18}$SiMe$_3$ | 48° C. | 5% | 3.5 | 5 | 14.4 | 513 | 9.1 |
| Me$_3$SiO(C$_{18}$H$_{37}$MeSiO)$_{54}$-(MeHSiO)$_{18}$SiMe$_3$ | 48° C. | 10% | 2.5 | — | 7.5 | 200 | — |
| Me$_3$SiO(C$_{18}$H$_{37}$MeSiO)$_{54}$-(MeHSiO)$_{18}$SiMe$_3$ | 48° C. | 15% | 3 | 75 | 2.6 | 522 | 13.4 |

As shown in Table 2, the Rheological properties of Elastic Modulus (G') and Dynamic Viscosity (n*) were evaluated for the various adhesive formulations at temperatures ranging from 50° C. to 200° C. The values were measured at temperatures utilized in the hot-melt process, a low boundary of 100° C. and a high temperature of 200° C. and were acceptable for both properties The alkylmethylsiloxane wax additive lowered the elastic modulus values compared to the Control PSA at both boundary temperatures.

The results displayed in Table 2 illustrate the overall desirable result of lowered dynamic viscosity of the Control PSA by the addition of the alkylmethylsiloxane waxes, in comparison to the Control PSA without wax, at temperatures of 50° C., 100° C., 150° C. and 200° C. Reduced dynamic viscosity was achieved for all wax-containing samples at or below 200° C.

Therefore, the objects of this invention have been met by adding alkylmethylsiloxane wax to a pressure sensitive silicone adhesive. By decreasing the dynamic viscosity of the adhesive, coatability was improved, which allows for less waste during manufacturing processes. Thus, there is provided in accordance with the present invention, a composition for an improved pressure sensitive adhesive and a method for coating the adhesive.

While our invention has been described in terms of a specific embodiment, it will be appreciated that other embodiments could readily be adapted by one skilled in the art. Accordingly, the scope of our invention is to be limited only by the following claims.

We claim:

1. A hot-melt, silicone pressure sensitive adhesive composition, comprising a mixture of (i) a silicate resin, (ii) a silicone fluid, and (iii) an alkylmethylsiloxane wax which decreases dynamic viscosity of the adhesive composition at temperatures equal to or below about 200° C.

2. The adhesive composition of claim 1, wherein the alkylmethylsiloxane wax is selected from the group consisting of waxes having the following formulations:

$$(RMeSiO)_x$$

TABLE 2

Rheological Data For Control PSA With Alkylmethylsiloxane Waxes At 50° C.-200° C.

| Wax Product | Wax MP | WT % Wax | 50° C. G' | 50° C. N* | 100° C. G' | 100° C. N* | 150° C. G' | 150° C. N* | 200° C. G' | 200° C. N* |
|---|---|---|---|---|---|---|---|---|---|---|
| Control PSA | — | — | 6.5E + 5 | 6.7E + 3 | 3.5E + 5 | 4.1E + 3 | 1.3E + 5 | 1.8E + 3 | 4.0E + 4 | 9.3E + 2 |
| (C$_{18}$H$_{32}$SiO)$_4$ | 38° C. | 1% | 3.5E + 5 | 4.1E + 3 | 1.0E + 5 | 1.5E + 3 | 2.8E + 4 | 4.7E + 2 | 6.5E + 3 | 1.3E + 2 |
| (C$_{18}$H$_{32}$SiO)$_4$ | 38° C. | 5% | 2.6E + 5 | 3.1E + 3 | 7.2E + 4 | 1.0E + 3 | 1.5E + 4 | 2.9E + 2 | 3.4E + 3 | 7.3E + 1 |
| (C$_{18}$H$_{32}$SiO)$_4$ | 38° C. | 10% | 5.5E + 5 | 5.9E + 3 | 1.9E + 5 | 1.8E + 3 | 6.3E + 4 | 9.7E + 2 | 2.7E + 4 | 5.0E + 2 |
| (C$_{18}$H$_{32}$SiO)$_4$ | 38° C. | 15% | 1.5E + 5 | 1.9E + 3 | 4.5E + 4 | 6.8E + 2 | 8.0E + 3 | 1.6E + 2 | 2.8E + 3 | 5.9E + 1 |
| (C$_{20}$H$_{34}$SiO)$_5$ | 53° C. | 1% | 4.8E + 5 | 5.2E + 3 | 1.7E + 5 | 2.2E + 3 | 4.5E + 4 | 7.2E + 2 | 1.5E + 4 | 2.9E + 2 |
| (C$_{20}$H$_{34}$SiO)$_5$ | 53° C. | 5% | 2.6E + 5 | 3.1E + 3 | 8.9E + 4 | 1.3E + 3 | 1.6E + 4 | 3.0E + 2 | 6.1E + 3 | 1.2E + 2 |
| (C$_{20}$H$_{34}$SiO)$_5$ | 53° C. | 10% | 4.9E + 5 | 5.4E + 3 | 2.2E + 5 | 3.0E + 3 | 7.1E + 4 | 1.1E + 3 | 1.9E + 4 | 3.9E + 2 |
| (C$_{20}$H$_{34}$SiO)$_5$ | 53° C. | 15% | 2.6E + 5 | 3.2E + 3 | 9.0E + 4 | 1.3E + 3 | 2.0E + 4 | 3.8E + 2 | 4.8E + 3 | 9.6E + 1 |
| (C$_{24-28}$H$_{49-57}$MeSiO)$_5$ | 56° C. | 1% | 4.0E + 5 | 4.5E + 3 | 1.5E + 5 | 2.0E + 3 | 3.5E + 4 | 6.1E + 2 | 1.2E + 4 | 2.4E + 2 |
| (C$_{24-28}$H$_{49-57}$MeSiO)$_5$ | 56° C. | 4% | 1.8E + 5 | 2.3E + 3 | 5.1E + 4 | 7.9E + 2 | 7.2E + 3 | 1.2E + 2 | 5.9E + 3 | 1.2E + 2 |
| (C$_{24-28}$H$_{49-57}$MeSiO)$_5$ | 56° C. | 5% | 2.0E + 5 | 2.5E + 3 | 6.0E + 4 | 9.1E + 2 | 9.2E + 3 | 1.6E + 2 | 5.4E + 3 | 1.1E + 2 |
| (C$_{24-28}$H$_{49-57}$MeSiO)$_5$ | 56° C. | 10% | 4.2E + 5 | 4.7E + 3 | 1.4E + 5 | 1.9E + 3 | 3.9E + 4 | 5.9E + 2 | 9.4E + 3 | 1.9E + 2 |
| (C$_{24-28}$H$_{49-57}$MeSiO)$_5$ | 56° C. | 15% | 3.5E + 5 | 4.0E + 3 | 6.2E + 4 | 9.1E + 2 | 1.6E + 4 | 1.6E + 2 | 4.1E + 3 | 8.5E + 1 |
| Me$_3$SiO(C$_{18}$H$_{37}$MeSiO)$_{54}$-(MeHSiO)$_{18}$SiMe$_3$ | 48° C. | 1% | 2.7E + 5 | 3.2E + 3 | 8.5E + 4 | 1.2E + 3 | 1.3E + 4 | 2.3E + 2 | 8.4E + 3 | 1.6E + 2 |
| Me$_3$SiO(C$_{18}$H$_{37}$MeSiO)$_{54}$-(MeHSiO)$_{18}$SiMe$_3$ | 48° C. | 4% | 2.5E + 5 | 3.0E + 3 | 8.2E + 4 | 1.2E + 3 | 1.2E + 4 | 1.6E + 2 | 8.1E + 3 | 1.6E + 2 |
| Me$_3$SiO(C$_{18}$H$_{37}$MeSiO)$_{54}$-(MeHSiO)$_{18}$SiMe$_3$ | 48° C. | 5% | 3.6E + 5 | 4.1E + 3 | 1.3E + 5 | 1.7E + 3 | 3.5E + 4 | 4.1E + 2 | 1.4E + 4 | 2.7E + 2 |
| Me$_3$SiO(C$_{18}$H$_{37}$MeSiO)$_{54}$-(MeHSiO)$_{18}$SiMe$_3$ | 48° C. | 10% | 5.2E + 5 | 5.6E + 3 | 2.4E + 5 | 2.9E + 3 | 8.9E + 4 | 1.2E + 3 | 2.9E + 4 | 5.0E + 2 |
| Me$_3$SiO(C$_{18}$H$_{37}$MeSiO)$_{54}$-(MeHSiO)$_{18}$SiMe$_3$ | 48° C. | 15% | 9.1E + 4 | 1.3E + 3 | 2.6E + 4 | 4.2E + 2 | 5.6E + 3 | 9.8E + 1 | 5.9E + 3 | 1.1E + 2 |

G' = Elastic storage modulus measured in dynes/cm$^2$.
N* = Dynamic viscosity measured in poise.

wherein R is $C_nH_{2n+1}$, Me is $CH_3$, $14 \leq n \leq 28$, and X is an integer from 4 to 6;

$RMe_2SiOSiMe_2R$ wherein Me is $CH_3$, R is $C_nH_{2n+1}$, and $n \geq 18$;

$RMe_2SiOSiMe_3$ wherein Me is $CH_3$, R is $C_nH_{2n+1}$, and $n \geq 24$;

$RMeSi(OSiMe_3)_2$ wherein Me is $CH_3$, R is $C_nH_{2n+1}$, and $n \geq 24$;

$Me_3SiO(RMeSiO)_x(R'MeSiO)_y SiMe_3$ wherein Me is $CH_3$, R is $C_nH_{2n+1}$, and $n \geq 18$, R' is H or $C_nH_{2n+1}$ and $n \geq 1$, when R' is H or $CH_3$ then the ratio of X:Y is greater than 1:3;

$RSiO_{3/2}$ wherein R is $C_nH_{2n+1}$, and $n \geq 1$; and mixtures thereof.

3. The adhesive composition of claim 1, wherein the alkylmethylsiloxane wax is present in an amount between about 1.0 and about 25.0 percent by weight based on total adhesive composition weight.

4. The adhesive composition of claim 1, wherein the alkylmethylsiloxane wax is present in an amount between about 5 percent and about 15 percent by weight based on total adhesive composition weight.

5. The adhesive composition of claim 1, wherein the silicone pressure sensitive adhesive containing the alkylmethylsiloxane wax has a dynamic viscosity less than or equal to 800 poise at a temperature equal to or below 200° C.

6. A hot-melt, silicone pressure sensitive adhesive composition, comprising:
   (a) between about 30 and about 70 percent by weight silicate resin;
   (b) between about 22 and about 60 percent by weight silicone fluid; and
   (c) between about 1.0 and about 25 percent by weight based of an alkylmethylsiloxane wax,
   all weight percents being based on total composition weight, and said alkylmethylsiloxane wax decreasing dynamic viscosity of the resultant adhesive composition at temperatures ranging from about 50° C. to about 200° C.

7. The adhesive composition of claim 6, wherein the alkylmethylsiloxane wax is selected from the group consisting of waxes having the following formulations:

$(RMeSiO)_x$ wherein R is $C_nH_{2n+1}$, Me is $CH_3$, $14 \leq n \leq 28$, and X is an integer from 4 to 6;

$RMe_2SiOSiMe_2R$ wherein Me is $CH_3$, R is $C_nH_{2n+1}$, and $n \geq 18$;

$RMe_2SiOSiMe_3$ wherein Me is $CH_3$, R is $C_nH_{2n+1}$, and $n \geq 24$;

$RMeSi(OSiMe_3)_2$ wherein Me is $CH_3$, R is $C_nH_{2n+1}$, and $n \geq 24$;

$Me_3SiO(RMeSiO)_x(R'MeSiO)_y SiMe_3$ wherein Me is $CH_3$, R is $C_nH_{2n+1}$, and $n \geq 18$, R' is H or $C_nH_{2n+1}$ and $n \geq 1$, when R' is H or $CH_3$ then the ratio of X:Y is greater than 1:3;

$RSiO_{3/2}$ wherein R is $C_nH_{2n+1}$, and $n \geq 1$; and mixtures thereof.

8. The adhesive composition of claim 1, wherein the silicate resin is a benzene-soluble resinous copolymer containing silicon-bonded hydroxyl radicals and consisting essentially of triorganosiloxy units of the formula $R_3SiO_{\frac{1}{2}}$ and tetra functional siloxy units of the formula $SiO_{4/2}$ in a ratio of about 0.6 to 0.9 triorganosiloxy units for each tetra functional siloxy unit present in the copolymer, wherein each R is a monovalent radical independently selected from the group consisting of hydrocarbon radicals of from 1 to 6 inclusive carbon atoms, and the silicone fluid is a silanol-endstopped polydiorganosiloxane fluid.

9. The adhesive composition of claim 1, wherein the silicate resin is a cohydrolysis product of a trialkyl hydrolyzable silane and an alkyl silicate, wherein the cohydrolysis product contains a plurality of silicon-bonded hydroxy groups, and the silicone fluid is a linear organopolysiloxane fluid containing silicon-bonded hydroxy groups.

10. A hot-melt, silicone pressure sensitive adhesive composition, comprising:
   a mixture of
   (i) between about 30 and about 70 percent by weight of a silicate resin,
   (ii) between about 22 and about 60 percent by weight of a silicone fluid, and
   (iii) between about 1.0 and about 25.0 percent by weight of an alkylmethylsiloxane wax which decreases the dynamic viscosity of the adhesive composition at temperatures equal to or below about 200° C., the alkylmethylsiloxane wax selected from the group consisting of waxes having the following formulations:

$(RMeSiO)_x$ wherein R is $C_nH_{2n+1}$, Me is $CH_3$, $14 \leq n \leq 28$, and X is an integer from 4 to 6;

$RMe_2SiOSiMe_2R$ wherein Me is $CH_3$, R is $C_nH_{2n+1}$, and $n \geq 18$;

$RMe_2SiOSiMe_3$ wherein Me is $CH_3$, R is $C_nH_{2n+1}$, and $n \geq 24$;

$RMeSi(OSiMe_3)_2$ wherein Me is $CH_3$, R is $C_nH_{2n+1}$, and $n \geq 24$;

$Me_3SiO(RMeSiO)_x(R'MeSiO)_y SiMe_3$ wherein Me is $CH_3$, R is $C_nH_{2n+1}$, and $n \geq 18$, R' is H or $C_nH_{2n+1}$ and $n \geq 1$, when R' is H or $CH_3$ then the ratio of X:Y is greater than 1:3;

$RSiO_{3/2}$ wherein R is $C_nH_{2n+1}$, and $n \geq 1$; and mixtures thereof, the percents by weight based on the total adhesive composition weight, the adhesive composition having a dynamic viscosity less than or equal to 800 poise at a temperature equal to or below 200° C.

* * * * *